United States Patent
Hughes

(10) Patent No.: US 12,392,746 B2
(45) Date of Patent: Aug. 19, 2025

(54) VOLUMETRIC MOISTURE CONTENT SENSOR

(71) Applicant: William C. Hughes, Woodstock, IL (US)

(72) Inventor: William C. Hughes, Woodstock, IL (US)

(73) Assignee: Innoquest, Inc., Woodstock, IL (US)

( * ) Notice: Subject to any disclaimer, the term of this patent is extended or adjusted under 35 U.S.C. 154(b) by 434 days.

(21) Appl. No.: 18/171,017

(22) Filed: Feb. 17, 2023

(65) Prior Publication Data

US 2024/0011929 A1 Jan. 11, 2024

Related U.S. Application Data

(60) Provisional application No. 63/473,920, filed on Jul. 5, 2022.

(51) Int. Cl.
| | |
|---|---|
| G01N 33/24 | (2006.01) |
| A01G 25/16 | (2006.01) |
| G01N 27/22 | (2006.01) |

(52) U.S. Cl.
CPC ............ *G01N 27/226* (2013.01); *A01G 25/16* (2013.01); *G01N 27/223* (2013.01)

(58) Field of Classification Search
CPC ... G01N 33/246; G01N 27/223; A01G 25/167
See application file for complete search history.

(56) References Cited

U.S. PATENT DOCUMENTS

| | | | |
|---|---|---|---|
| 2005/0120813 A1* | 6/2005 | Clark | G01N 3/40 73/866.5 |
| 2016/0183484 A1* | 6/2016 | Richings, Sr. | A01G 25/167 239/11 |
| 2020/0150067 A1* | 5/2020 | Ruys | G01N 33/246 |

* cited by examiner

*Primary Examiner* — Herbert K Roberts
(74) *Attorney, Agent, or Firm* — Reinhart Boerner Van Deuren P.C.

(57) ABSTRACT

An apparatus for measuring volumetric moisture content using an affixing method for sensing probes that reduces bending and breaking stress on the probes. The volumetric moisture content sensor has sensing probes secured against compressive axial movement during insertion into a test media, while allowing limited radial movement. Radial movement is limited via the use of a compressed elastomeric sleeve surrounding the portion of the rod supported by the sensor housing. When in the uncompressed state, there is a clearance fit allowing free movement for removal and replacement of the probes. The compressed elastomeric sleeve is used in conjunction with a rod support mechanism such that the sleeve seals out moisture, dust, and other contaminants from an interior portion of the sensor. The compressed elastomeric sleeve provides a force that assures a proper electrical connection between the sensor probes and an electronic circuit of the sensor.

23 Claims, 3 Drawing Sheets

VOLUMETRIC MOISTURE CONTENT SENSOR

CROSS-REFERENCE TO RELATED APPLICATIONS

This patent application claims the benefit of U.S. Provisional Patent Application No. 63/473,920, filed Jul. 5, 2022, the entire teachings and disclosure of which are incorporated herein by reference thereto.

FIELD OF THE INVENTION

The present invention is in the technical field of moisture content measurement. More particularly, the present invention is in the technical field of volumetric moisture content of soil, growing media, and other homogeneous or nonhomogeneous agricultural products. More particularly, the present invention is in the technical field of a method for attachment of sensing probes to such a volumetric moisture content meter.

BACKGROUND OF THE INVENTION

Water content or moisture content is important to the growth of plants as well as the safe storage of raw and refined agricultural products. There are many techniques to measure the moisture content of a substance. Most generally these can be broken down into gravimetric (mass based) or volumetric measurements. Volumetric measurements have the advantage of accounting for air or pore space in a media like soil, and therefore more readily relate to understanding the quantity of water available within the root zone of the plant. It is desirable to make such volumetric moisture content readings in the field without disturbing the growth of any roots or plants within or near the test area.

Many electronic instruments have been developed to measure volumetric moisture content based on the high ratio of the dielectric constant of water (approx. 80) to that of dry soil and air (approx. 1-3). Such instruments employ circuits that measure this dielectric constant via capacitance, wave propagation through a transmission line, or wave propagation reflected from the end of an open transmission line. In all cases, it is desirable to place the electrodes that make up the transmission line or the plates of the capacitor directly into the media being measured. The use of rods protruding from the sensor head has proven to be a highly effective way to produce such a sensor, which is easily inserted into the test media.

Therefore, it is important to anyone who uses such a device that the rods be abrasion resistant, corrosion resistant, and break resistant. To function correctly, they must also be electrically conductive. Such rods are typically manufactured from stainless steel to meet all these requirements. Since small diameter rods require less force to insert into the media being tested and disturb the media less, they are preferred. The drawback to smaller diameter rods is that they are more prone to bending. The base of the sensor rods is typically attached or fixed to a ridged support on the sensor. As a result, any flexing of the rods imparts a large concentration of bending stress at this attachment point.

Bending therefore occurs at this high stress point and can result in breaking of the rods after repeated bending and straightening cycles as the user attempts to correct distortion of the rods when rocks or other discontinuities on the media cause rod flexing during insertion.

It would therefore be desirable to have a portable apparatus for measuring volumetric moisture content by electronic means requiring protruding rods that are not as prone to bending when objects are struck during use. Embodiments of the present invention provide such a means to limit bending and/or breaking of these sensor rods compared to the current methods employed.

BRIEF SUMMARY OF THE INVENTION

In one aspect, embodiments of the present invention provide a volumetric moisture content sensor that includes a sensor head with a circuit for determining the water content of a media. The circuit is disposed in a sensor housing with a plurality of sensor probes that are removably attached to the sensor housing and protrude outward from the sensor housing. In a particular embodiment, each of the plurality of sensor probes is configured for insertion into the media. Additionally, at least one of the plurality of sensor probes has an elastomeric sleeve arranged to absorb stress caused by movement of a respective sensor probe.

In a particular embodiment, a function of the sensor head is activated via an electronic display, an electronic controller, a smartphone, a smartwatch, or a computer. In a further embodiment, the electronic display is electrically connected to the sensor head through a support pole. In a further embodiment, the support pole includes bonding wires that electrically connect the sensor head to the electronic display. The support pole is connected at its proximal end to the electronic display and its distal end to the sensor head. In an alternative embodiment, the electronic display is attached to the distal end of the support pole. In a further embodiment, a wireless transmitter is configured to transmit data from the volumetric moisture content sensor to the display for one of a smartphone, a smartwatch, an electronic controller, or a computer.

In a particular embodiment, the sensor housing includes an upper sensor housing and a lower sensor housing. Additionally, the upper sensor housing and the lower sensor housing are configured to form a single continuous body.

In a particular embodiment, the circuit is mounted within the upper sensor housing and electrically connected to the plurality of sensor probes, and a removable retaining cap is mounted to the lower sensor housing.

In a particular embodiment, the circuit is mounted to the upper sensor housing using one or more screws. Additionally, each of the one or more screws is configured to provide an electrical connection between one of the plurality of sensor probes and the circuit. In a further embodiment, the circuit is configured to provide a signal that is transmitted through the plurality of sensor probes in the media.

In a particular embodiment, the retaining cap includes a threaded ring and a fixed end plate. The end plate fits into the threaded ring and has holes therein to accommodate the plurality of sensor probes. In some embodiments, a perimeter portion of the end plate has a lip or edge geometry configured to retain the end plate inside the threaded ring. Additionally, the threaded ring rotates relative to the end plate. In a particular embodiment, the threaded ring has an annular convex surface, and the edge geometry is a concave surface that extends around the perimeter portion, and seats around the annular convex surface.

In some embodiment, the volumetric moisture content sensor includes a temperature sensor that protrudes from inside of the sensor housing through the retaining cap and can determine a media temperature.

In a particular embodiment, each of the plurality of sensor probes has a cylindrical shaft with a pointed tip at a first end and a radially-extending head at a second end opposite the first end. The pointed tip is configured for insertion into the media.

In a particular embodiment, the elastomeric sleeve is assembled onto the cylindrical shaft. In a further embodiment, the radially-extending head has a diameter greater than that of the cylindrical shaft to provide a surface for the elastomeric sleeve to push against.

In a particular embodiment, the sensor housing includes a plurality of tubular linings, each disposed within a hole in the lower sensor housing. In a further embodiment, each of the holes is sized to accommodate the radially-extending head of one of the plurality of sensor probes.

In a particular embodiment, each of the plurality of tubular linings comprises Teflon®. However, in alternative embodiments, the plurality of tubular linings may also comprise a low coefficient of friction material.

In a particular embodiment, the elastomeric sleeve is configured to deform when compressed along an axial direction. In a further embodiment, the elastomeric sleeve is capable of absorbing stress from the deflection of one of the plurality of sensor probes in a direction perpendicular to a longitudinal axis of the cylindrical shaft. This arrangement permits the elastomeric sleeve to seal out moisture, dust, and other contaminants from an interior portion of the volumetric moisture content sensor and, more specifically, from an interior portion of the lower sensor housing. In the embodiments shown, the elastomeric sleeve may be a synthetic rubber material or a natural rubber material.

In a particular embodiment, the volumetric water content sensor provides a means to limit and/or prevent bending or breaking of protruding sensor rods that form either a transmission line or capacitor as part of the electronic moisture sensing method. The invention comprises metal sensor rods affixed to the sensor/meter via a material that allows them to flex in any lateral or radial direction without causing permanent deflection of the metal rods or fixing material. With this manner of construction, the rods are allowed to flex when encountering a rock or other anomaly in the test media during their insertion. Once withdrawn, the rods return to their true position as the flexible affixing media returns to its neutral state.

Embodiments of the volumetric water content sensor also use the flexible affixing media to assert an axial force on the sensor rods to assure electrical contact between the rods and the electronic sensing circuit. This feature of the invention assures electrical contact is maintained throughout the flexing and subsequent return to neutral of the sensor rods.

Other aspects, objectives, and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, and serve to explain the principles of the invention. In the drawings.

While the invention will be described in conjunction with certain preferred embodiments, there is no intent to limit it to these embodiments. On the contrary, the intent is to cover all alternatives, modifications and equivalents as indicated within the spirit and scope of the invention as defined by the appended claims.

DETAILED DESCRIPTION

Figure 1:
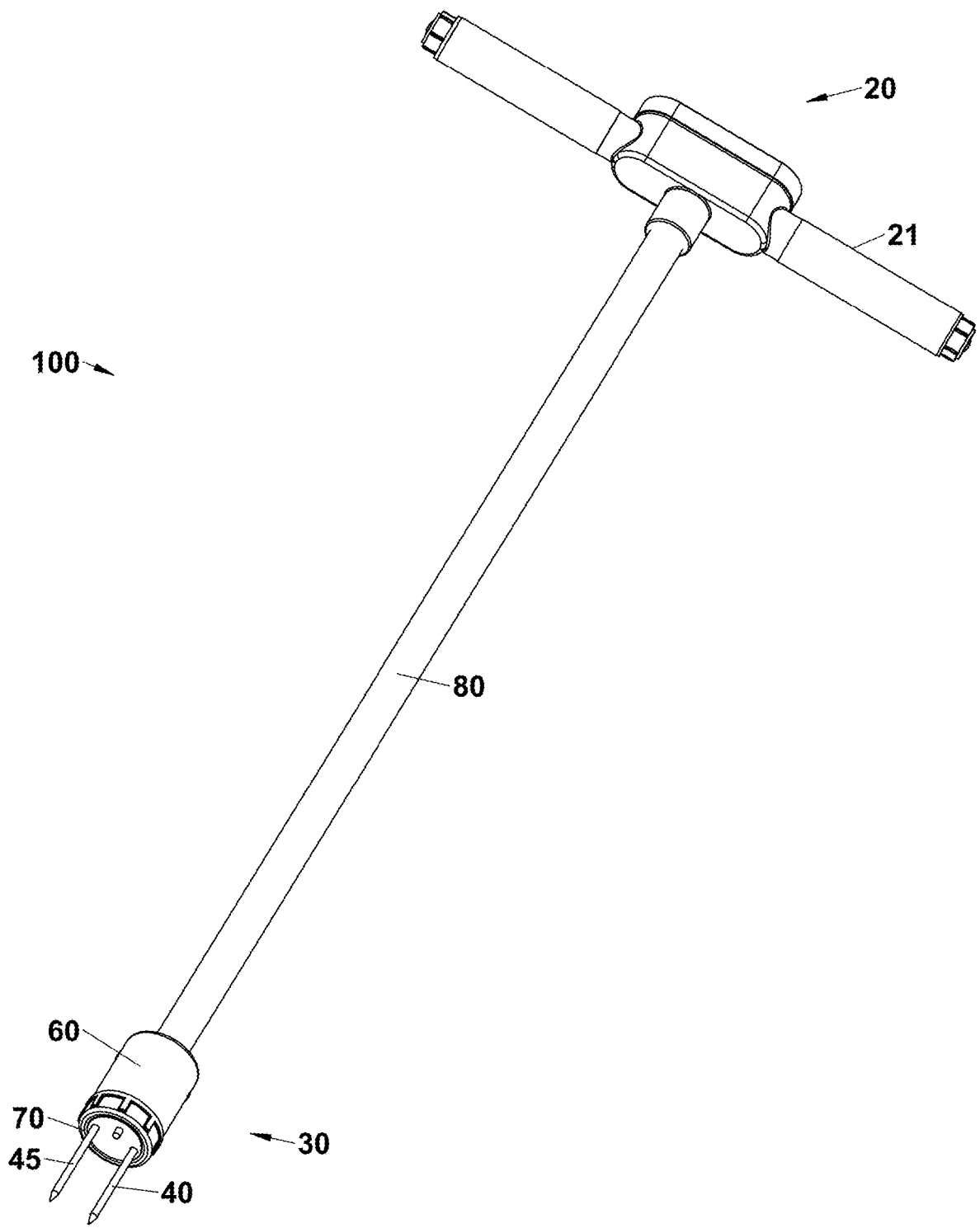
FIG. 1 is a perspective view of a volumetric water content sensor, in accordance with an embodiment of the invention.
Figure 2:
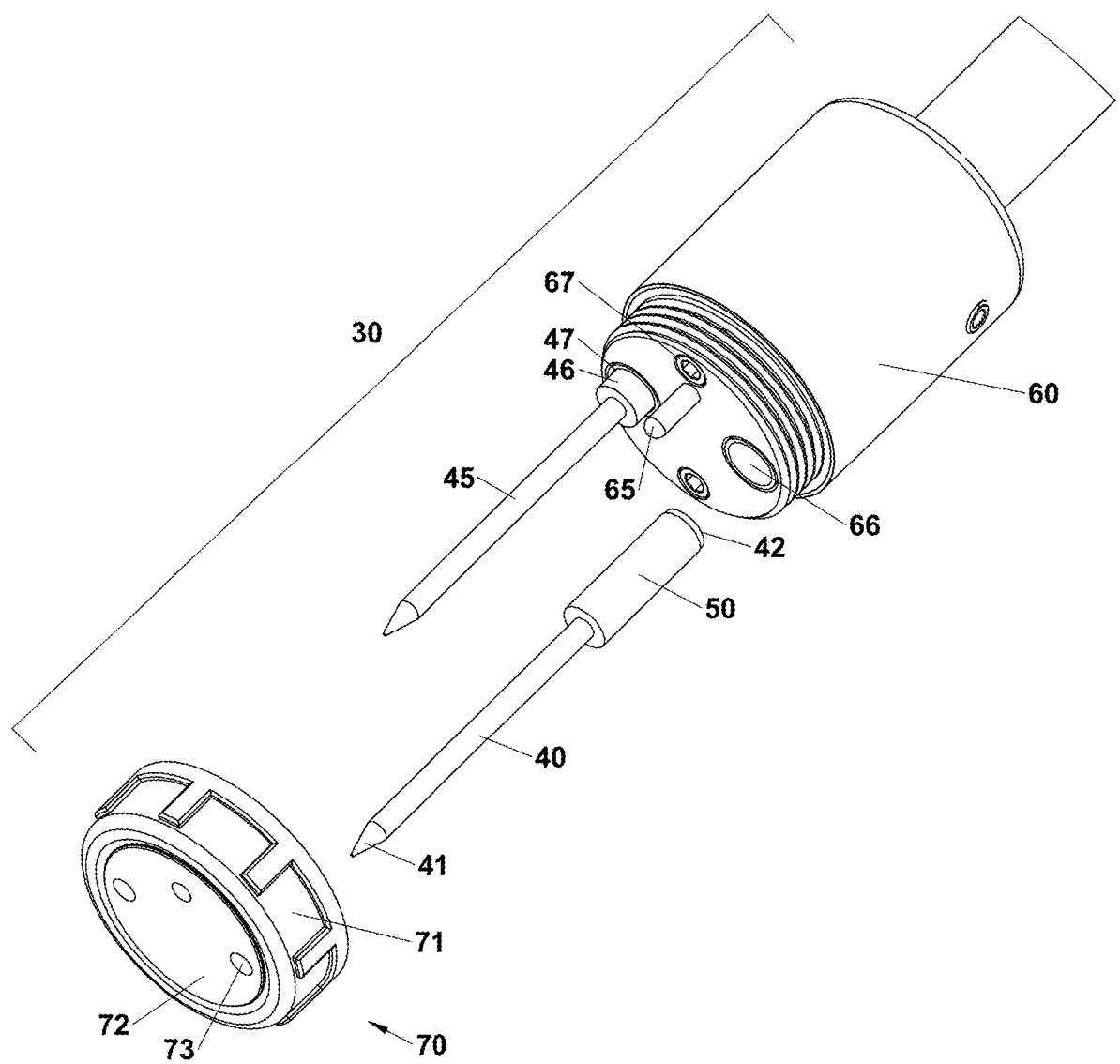
FIG. 2 is a partially exploded perspective view of the sensor shown in FIG. 1, according to an embodiment of the invention.
Figure 3:
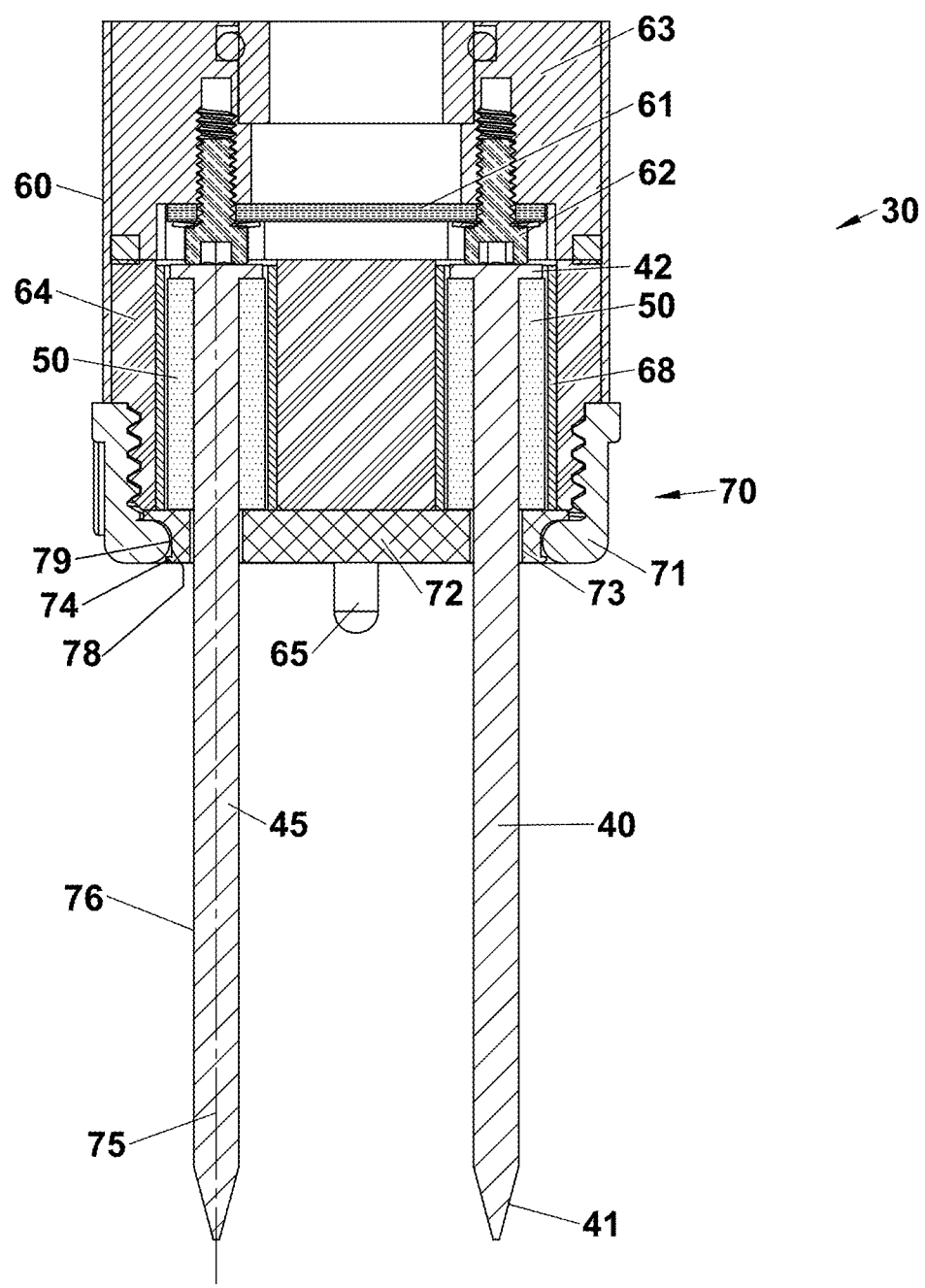
FIG. 3 is a cross-sectional view of the portion shown in FIG. 2, in accordance with an embodiment of the invention.

A volumetric water content sensor 100 for determining volumetric moisture content, constructed in accordance with an embodiment of the invention, is shown in FIGS. 1-3. This preferred embodiment comprises an electronic display portion 20, a support pole 80, and a moisture sensor portion 30, as shown in FIGS. 1-3.

A particular embodiment of the volumetric water content sensor 100 functions in the following manner. The user first activates the electronic display 20, which then starts the electronic function of the sensor head 30, which in the case of the illustrated embodiment is attached to the display 20 via support pole 80 that contains connection wires. The support pole is connected at its proximal end to the electronic display and its distal end to the sensor head. However, in an alternative embodiment, the electronic display is attached to the distal end of the support pole. In a further embodiment, the user may activate the sensor head 30 via an electronic controller, a smartwatch, a smartphone, or a computer, such as a tablet, laptop, or desktop computer. The user then inserts probe rods 40, 45 into the media being tested, such as soil, growing media, or other moisture containing media, such as agricultural products, for example.

An electronic circuit on circuit board 61 in sensor head 30 then detects the volumetric moisture content by sending electronic signals to and/or from probe rods 40, 45. This moisture dependent sensed signal is then transmitted back to the display portion 20 via wires inside support pole 80. This moisture content information is then displayed to the user directly, and/or stored in the unit's memory, and/or transmitted by some means to an external display or storage device like a computer, an electronic controller, or smartphone, or smartwatch. As used herein, the term "computer" includes tablet computers, laptop computers, desktop computers, and notebook computers.

Alternatively, the embodiment may include a wireless transmitter for transmitting the moisture content information or other data from the volumetric water content sensor 100 to a display of one of the aforementioned external display devices. As described, the probe rods 40, 45 can be withdrawn from one location in the media and inserted in another location to check moisture at that new location as many times as necessary to characterize the media's volumetric moisture content.

Referring to FIGS. 2-3, sensor head 30 is comprised of sensor housing 60, electronic circuit 61, probe rods 40, 45, and retaining cap 70. Sensor head 30 is designed to be mounted on the end of support pole 80 allowing the user to measure moisture contents of media at ground level and have the display portion 20 with handles 21 at a convenient working height for the user. The embodiment shown has circuit board 61 attached to the upper sensor housing 63 with mounting screws 62. Mounting screws 62 also function to make electrical connections between sensor electrodes 40, 45, and electrical pads on circuit board 61.

Retaining cap 70 attaches to lower sensor housing 64 and retains sensor probes 40, 45 such that they cannot be removed from sensor housing 60. Retaining cap 70 also functions to apply a compressive force to elastomeric sleeve 50. When this axial compressive force is applied to elastomeric sleeve 50, it expands in a radial direction to fill the inside of cavity 66 thereby semi rigidly fixing electrodes 40, 45 to lower sensor housing 64. Lower sensor housing 64 is attached to upper sensor housing 63 via screws 67. In this way, lower sensor housing 64 and upper sensor housing 63 become one body, shown in FIG. 2 as sensor housing 60. The embodiment shown also has a temperature sensor 65 that protrudes through retaining cap 70 for measurement of test media temperature in addition to moisture content measurements.

Referring to FIGS. 1-3, sensor probes 40, 45 are identical in the preferred embodiment but could be of varying length or size and could be present in different quantities in other embodiments. In a particular embodiment, electrodes 40, 45 each have a cylindrical shaft 76 with a pointed tip 41 at a first end of the cylindrical shaft 76, and a radially-extending head 42 at a second end cylindrical shaft 76 opposite the first end. Pointed tip 41 helps to lower the insertion force when the sensor electrodes 40, 45 are inserted into the media being tested for moisture content. The flat head 42 has a diameter greater than that of cylindrical shaft 76 and provides a surface for elastomeric sleeve 50 to push against, therefore restricting sensor probes 40, 45 from being able to be drawn through the inside of said sleeve 50.

It is understood that other geometries for the ends or middle of sensor probes 40, 45 could accomplish similar functions in alternate embodiments. In a particular embodiment, sensor probes 40, 45 are constructed of stainless steel, which meets the requirements of good electrical conductivity, good corrosion resistance, good abrasion resistance, and resistance to bending. It is understood that other materials will also meet these requirements and could be substituted. In certain embodiments, sensor probes 40, 45 are common stainless-steel nails used in timber construction industry and therefore available at minimal cost compared to custom fabricated probes of similar geometry.

Again, referring to FIGS. 2 and 3, elastomeric sleeve 50 is described in more detail. Elastomeric sleeve 50 can be loose fitting around sensor probes 40, 45, or loose fitting inside hole 66, or loose fitting on both sensor probes 40 and hole 66 when in an uncompressed state. Compressing elastomeric sleeve 50 along its axial direction will cause deformation, which expands it in the radial dimension. In a particular embodiment, elastomeric sleeve 50 absorbs stress from deflection of sensor probes 40, 45 in a direction perpendicular to a longitudinal axis 75 of cylindrical shaft 76. In a particular embodiment, elastomeric sleeve 50 is configured to deform when compressed along its axial direction. Typically, elastomeric sleeve 50 has a length slightly greater length than that of lower sensor housing 64, and is therefore compressed when removable retaining cap 70 is assembled to lower sensor housing 64.

In this example, as removable retaining cap 70 is threaded onto lower sensor housing 64, elastomeric sleeve 50 compresses axially and expands radially around cylindrical shaft 76. In this context, "axially" refers to a longitudinal axis of elastomeric sleeve 50, which is the same as longitudinal axis 75 of cylindrical shaft 76. Sufficient axial compression and radial expansion results in a firm and tight fit of elastomeric sleeve 50 on both the outer diameter of sensor probes 40, 45 and inner diameter of hole 66. This results in a firm mechanical connection between sensor probes 40, 45 and hole 66 of the lower sensor housing 64, as shown in FIG. 2, and protects sensor probes 40, 45 from damage and stress that might otherwise occur due to lateral movement of the probes 40, 45 in directions perpendicular to longitudinal axis 75. This configuration enables the elastomeric sleeve 50 to shield the interior portion of the lower sensor housing 64 from moisture, dust, and other contaminants, thereby ensuring the accuracy and durability of the volumetric water content sensor 100. In the embodiment shown, the sensor probes 40, 45 are essential for measuring moisture content, and must maintain a proper electrical connection to the circuit board 61. The elastomeric sleeve 50 acts as a barrier, preserving the integrity of that electrical connection and protecting the interior portion of the lower sensor housing 64 from external elements that could cause corrosion, damage, or interference with the aforementioned connection.

In a particular embodiment, elastomeric sleeve 50 is press-fit onto sensor probes 40, 45 and has a clearance or loose fit into hole 66, as shown by clearance gap 47 in FIG. 2. This loose fit into hole 66 allows for easy insertion and removal of probes 40, 45 from sensor housing 60 when changing probes 40, 45 is necessary. Probes 40, 45 can be changed to accommodate probes of different lengths or when existing probes become worn or damaged. Elastomeric sleeve 50 can be constructed of any resilient material, which returns to its original shape after being deformed by displacement. This is typically a synthetic or natural rubber material. In certain embodiments, elastomeric sleeve 50 is constructed of Viton® or urethane rubber.

With reference to FIG. 3, hole 66 of FIG. 2 is described in more detail. As previously mentioned, hole 66 is meant to receive elastomeric sleeve 50 when sensor probes 40, 45 is assembled to sensor head 30. Elastomeric sleeve 50 is then axially compressed to form a firm radial connection around sensor probes 40, 45. During the compression, an extra protruding length 46 of FIG. 2 of elastomeric sleeve 50 is forced into hole 66 until flush with the end of sensor housing 60, as shown in FIG. 3. As this compression occurs elastomeric sleeve 50 slides along the inner wall of hole 66 to allow compression of the sleeve 50 along its entire length.

This axial sliding of elastomeric sleeve 50 along the wall of hole 66 is enhanced by reduced friction between the interface of these two sliding materials. It is therefore helpful to have a low coefficient of friction on the surface of one or both of these materials. Coatings or lubricants can accomplish the goal of a low coefficient of friction between these materials. Selecting one of the materials to have a low coefficient of friction will also accomplish this goal. Elastomeric materials typically do not have a low coefficient of friction and materials with low coefficient of friction for the sensor body are typically of higher relative cost and do not provide as high of physical strength. Some preferred embodiments facilitate this low coefficient of friction by selecting a high-strength plastic or metal material for the lower sensor housing 64 with a tubular lining 68, as shown in FIG. 3. In certain embodiments, elastomeric sleeve 50 is press-fit into hole 66 such that the inside diameter of hole 66 is virtually the same as the outside diameter of tubular lining 68. In a particular embodiment, this tubular lining 68 is made from of Teflon® or a similar low-coefficient-of-friction material.

Now referring to FIGS. 2 and 3, retaining cap 70 is described in more detail. Retaining cap 70 is comprised of threaded ring 71 and end plate 72 in the embodiment shown. End plate 72 includes holes 73 for sensor probes 40, 45 to pass through. The diameter of holes 73 is selected to be larger than the outside diameter of sensor probes 40, 45, so that radial movement of said probes 40, 45 is possible without causing the sensor probes 40, 45 to come into contact with holes 73 of end plate 72. It is understood that a sufficient amount of radial movement of sensor probes 40, 45 will always allow contact between the probes 40, 45 and edges of the holes 73.

The design of volumetric water content sensor 100, and specifically of sensor housing 60 is such that, as the radial displacement of sensor probes 40, 45 increases, the deformation of elastomeric sleeve 50 allows for sufficient movement of sensor probes 40, 45 during insertion into the test media. This design allows for displacement of sensor probes 40, due to embedded rocks or obstructions without causing permanent damage or deformation in sensor probes 40, 45.

In a particular embodiment, threaded ring 71 screws onto a mating thread on lower sensor housing 64. End plate 72 fits into threaded ring 71 with enough clearance to allow the threaded ring 71 to be screwed into place while spinning around end plate 72. Preferably, end plate 72 is configured to remain inside the threaded ring 71, allowing the threaded ring 71 to rotate relative to end plate 72. Threaded ring 71 overlaps a portion of end plate 72 such that as threaded ring 71 is screwed onto lower sensor housing 64 end plate 72 is forced against elastomeric sleeve 50 and causes it to compress in the axial direction.

A further feature of end plate 72 is that, in some embodiments, a perimeter portion of end plate 72 has a lip or edge geometry 74, which retains this plate inside threaded ring 71, so that when retaining cap 70 is removed from lower sensor housing 64, end plate 72 does not separate from threaded ring 71, thereby limiting the number of parts that can be misplaced or dropped while the user is changing sensor probes 40, 45. In a particular embodiment, threaded ring 71 has an annular convex surface 79. End plate 72 has edge geometry 74 and concave surface 78 that extends around the perimeter portion, and seats around the annular convex surface 79. It is understood that retaining cap 70 may be comprised of components, such as threaded ring 71 and end plate 72 or more parts, which may be of plastic or metal.

In a particular embodiment, all components of end cap 70 are plastic with low moisture absorption characteristics. It is further understood the end cap 70 could be affixed to sensor housing 60 with latches, screws, ramps, or cams to perform the functions as mentioned above. While a particular embodiment of the invention has been described in detail above, it should also be understood that alternate embodiments of volumetric water content sensor 100 may have more than two sensor probes 40, 45. In a further embodiment of the invention, there may be only one sensor probes 40 or more than two probes 40, 45, with any number or combination of them affixed in the method described by this invention. It is also recognized that the method of compressing the elastomeric support material could be by other means of fastener, latch, or cam.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A volumetric moisture content sensor comprising:
   a sensor head having a circuit for determining water content for a media, the circuit disposed in a sensor housing having a plurality of sensor probes protruding outward from the sensor housing, the plurality of sensor probes configured for insertion into the media;
   wherein at least one of the plurality of sensor probes has an elastomeric sleeve arranged to absorb stress caused by movement of the at least one of the plurality of sensor probes.

2. The volumetric moisture content sensor of claim 1, wherein a function of the sensor head is activated via an electronic display, an electronic controller, a smartphone, a smartwatch, or a computer.

3. The volumetric moisture content sensor of claim 2, wherein the electronic display is electrically connected to the sensor head through a support pole, the support pole having a proximal end attached to the electronic display and a distal end attached to the sensor head.

4. The volumetric moisture content sensor of claim 3, wherein the support pole includes bonding wires that electrically connect the sensor head to the electronic display.

5. The volumetric moisture content sensor of claim 2, further comprising a support pole having a proximal end with handles for a user and a distal end with the sensor head and electronic display attached thereto.

6. The volumetric moisture content sensor of claim 1, further comprising a wireless transmitter configured to transmit data from the volumetric moisture content sensor to a display for one of a smartwatch, smartphone, an electronic controller, or a computer.

7. The volumetric moisture content sensor of claim 1, wherein the sensor housing includes an upper sensor housing and a lower sensor housing, wherein the circuit is mounted within the upper sensor housing and electrically connected to the plurality of sensor probes, wherein a removable retaining cap is mounted to the lower sensor housing.

8. The volumetric moisture content sensor of claim 7, wherein the circuit is mounted to the upper sensor housing using one or more screws, wherein each of the one or more screws is configured to provide an electrical connection between one of the plurality of sensor probes and the circuit.

9. The volumetric moisture content sensor of claim 7, wherein the upper sensor housing and the lower sensor housing are configured to form a single continuous body.

10. The volumetric moisture content sensor of claim 7, wherein the retaining cap includes a threaded ring and a fixed end plate, wherein the end plate fits into the threaded ring and has holes therein to accommodate the plurality of sensor probes.

11. The volumetric moisture content sensor of claim 10, wherein a perimeter portion of the end plate has a lip or edge geometry configured to retain the end plate inside the threaded ring, wherein the threaded ring rotates relative to the end plate.

12. The volumetric moisture content sensor of claim 11, wherein the threaded ring has an annular convex surface, and the edge geometry is a concave surface that extends around the perimeter portion, and seats around the annular convex surface.

13. The volumetric moisture content sensor of claim 1, further including a temperature sensor capable of determining a media temperature, the temperature sensor protruding from inside of the sensor housing through the retaining cap.

14. The volumetric moisture content sensor of claim 1, wherein each of the plurality of sensor probes has a cylindrical shaft with a pointed tip at a first end and a radially-extending head at a second end opposite the first end, wherein the pointed tip is configured for insertion into the media.

15. The volumetric moisture content sensor of claim 14, wherein the elastomeric sleeve is assembled onto the cylindrical shaft, wherein the radially-extending head has a diameter greater than that of the cylindrical shaft, the radially-extending head configured to provide a surface for the elastomeric sleeve to push against.

16. The volumetric moisture content sensor of claim 15, wherein the elastomeric sleeve is configured to deform when compressed along an axial direction, the sleeve having a length such that the elastomeric sleeve compresses axially and expands radially when a removable retaining cap is assembled to the sensor housing.

17. The volumetric moisture content sensor of claim 14, the sensor housing further including a plurality of tubular linings, each tubular lining disposed within an opening in the lower sensor housing.

18. The volumetric moisture content sensor of claim 17, wherein each of the openings is sized to accommodate the radially-extending head of one of the plurality of sensor probes.

19. The volumetric moisture content sensor of claim 1, wherein the elastomeric sleeve absorbs stress from deflection of one of the plurality of sensor probes in a direction perpendicular to a longitudinal axis of the cylindrical shaft.

20. The volumetric moisture content sensor of claim 1, wherein each of the plurality of sensor probes is removably attached to the sensor housing.

21. The volumetric moisture content sensor of claim 1, wherein the circuit housed in the sensor head is configured to provide a signal that is transmitted through the plurality of sensor probes into the media.

22. The volumetric moisture content sensor of claim 1, wherein the elastomeric sleeve is made from a synthetic rubber material or a natural rubber material.

23. The volumetric moisture content sensor of claim 1, wherein the elastomeric sleeve is configured to seal out moisture, dust, and other contaminants from an interior portion of the volumetric moisture content sensor.

* * * * *